United States Patent
Bowman et al.

(10) Patent No.: US 10,994,073 B2
(45) Date of Patent: May 4, 2021

(54) LABELING SYSTEM AND METHOD FOR PORTS IN INTRAVENOUS SYSTEMS

(71) Applicant: Frazbo, LLC, Millcreek, UT (US)

(72) Inventors: Stacie L. Bowman, Millcreek, UT (US); Lori Frazier, Salt Lake City, UT (US)

(73) Assignee: Frazbo LLC, Millcreek, UT (US)

( * ) Notice: Subject to any disclaimer, the term of this patent is extended or adjusted under 35 U.S.C. 154(b) by 0 days.

(21) Appl. No.: 16/513,649

(22) Filed: Jul. 16, 2019

(65) Prior Publication Data

US 2020/0038581 A1  Feb. 6, 2020

Related U.S. Application Data

(60) Provisional application No. 62/699,496, filed on Jul. 17, 2018.

(51) Int. Cl.
  *A61M 5/14* (2006.01)
  *G09F 3/18* (2006.01)

(52) U.S. Cl.
  CPC .............. *A61M 5/14* (2013.01); *G09F 3/18* (2013.01); *A61M 2205/60* (2013.01)

(58) Field of Classification Search
  CPC ............ A61M 39/165; A61M 39/0247; A61M 39/18; A61M 25/0097; A61M 2039/0258; A61M 2039/0288; A61M 2209/06; A61F 13/38
  See application file for complete search history.

(56) References Cited

U.S. PATENT DOCUMENTS

| | | | | |
|---|---|---|---|---|
| 4,037,599 | A | * | 7/1977 | Raulerson ............ A61M 5/1582 604/44 |
| 5,224,674 | A | * | 7/1993 | Simons ................. F16L 3/2235 248/68.1 |
| 5,389,082 | A | * | 2/1995 | Baugues ............. A61M 5/1418 128/DIG. 26 |
| 6,217,564 | B1 | * | 4/2001 | Peters ................ A61M 39/1011 604/111 |
| 6,361,523 | B1 | * | 3/2002 | Bierman ............... A61M 25/02 128/DIG. 26 |
| 6,613,012 | B2 | * | 9/2003 | Kraushaar ............... A61M 5/14 40/630 |
| 6,951,550 | B2 | * | 10/2005 | Bierman ............... A61M 25/02 128/DIG. 26 |

(Continued)

OTHER PUBLICATIONS

StatLock Foley Stabilization Device Product Instructions, C.R. Bard, Inc., apparently printed May 2017, pp. 1-2.

*Primary Examiner* — Cassandra Davis
(74) *Attorney, Agent, or Firm* — Warren M. Pate; Pate Peterson, PLLC (57) ABSTRACT

A method of labeling an intravenous (IV) system is disclosed. The method may begin with obtaining a label. A label may be formed of a polymeric material and include a top, a bottom, and an aperture formed in at least one of the top and the bottom. At least one of the top and the bottom may have an exterior surface. The label may be applied to an IV system by closing the top with respect to the bottom such that at least one of tubing or a port of the IV system is secured within the aperture. A medical professional may then write on the exterior surface of the label a name of a medication to be administered through the IV system.

20 Claims, 13 Drawing Sheets

(56) References Cited

U.S. PATENT DOCUMENTS

| | | | | |
|---|---|---|---|---|
| 7,455,662 B2* | 11/2008 | Kraushaar | ............... | A61M 5/14 |
| | | | | 40/660 |
| 8,246,600 B2* | 8/2012 | Raulerson | ......... | A61M 25/0026 |
| | | | | 604/508 |
| 8,516,727 B1* | 8/2013 | Maraia | .................... | G09F 3/205 |
| | | | | 40/316 |
| 9,480,821 B2* | 11/2016 | Ciccone | ................ | A61M 25/02 |
| D790,057 S * | 6/2017 | Ashman-Stauss | ........... | D24/130 |
| 9,981,111 B2* | 5/2018 | Friedrich | .............. | A61M 25/02 |
| 10,283,950 B2* | 5/2019 | Gintz | ....................... | H02G 3/32 |
| 2008/0027395 A1* | 1/2008 | Rintel | ................ | A61G 7/0503 |
| | | | | 604/192 |
| 2014/0100533 A1* | 4/2014 | Lyons | ................ | A61M 39/20 |
| | | | | 604/264 |
| 2015/0144746 A1* | 5/2015 | Stewart | ............... | A61M 5/1418 |
| | | | | 248/67.5 |
| 2015/0262515 A1* | 9/2015 | Leonardis | ............... | G09F 3/205 |
| | | | | 40/316 |
| 2018/0361133 A1* | 12/2018 | Herron | .............. | A61M 39/0247 |

* cited by examiner

LABELING SYSTEM AND METHOD FOR PORTS IN INTRAVENOUS SYSTEMS

THE RELATED APPLICATIONS

This application claims the benefit of U.S. Provisional Patent Application Ser. No. 62/699,496 filed Jul. 17, 2018, which is hereby incorporated by reference.

BACKGROUND

1. The Field of the Invention

This invention relates to intravenous systems and, more particularly, to novel systems and methods for securing and labeling access ports in intravenous systems.

2. The Background Art

Intravenous (IV) therapy involves delivering liquids directly into a vein of a patient. The liquids delivered in IV therapy may facilitate hydration, delivery of one or more medications, or the like. There are certain risks associated with properly setting up and administering IV therapy. Accordingly, what are needed are systems and methods that reduce those risks.

BRIEF DESCRIPTION OF THE DRAWINGS

The foregoing features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DETAILED DESCRIPTION OF SELECTED EMBODIMENTS

It will be readily understood that the components of the present invention, as generally described and illustrated in the drawings herein, could be arranged and designed in a wide variety of different configurations. Thus, the following more detailed description of the embodiments of the system and method of the present invention, as represented in the drawings, is not intended to limit the scope of the invention, as claimed, but is merely representative of various embodiments of the invention. The illustrated embodiments of the invention will be best understood by reference to the drawings, wherein like parts are designated by like numerals throughout.

Figure 1:
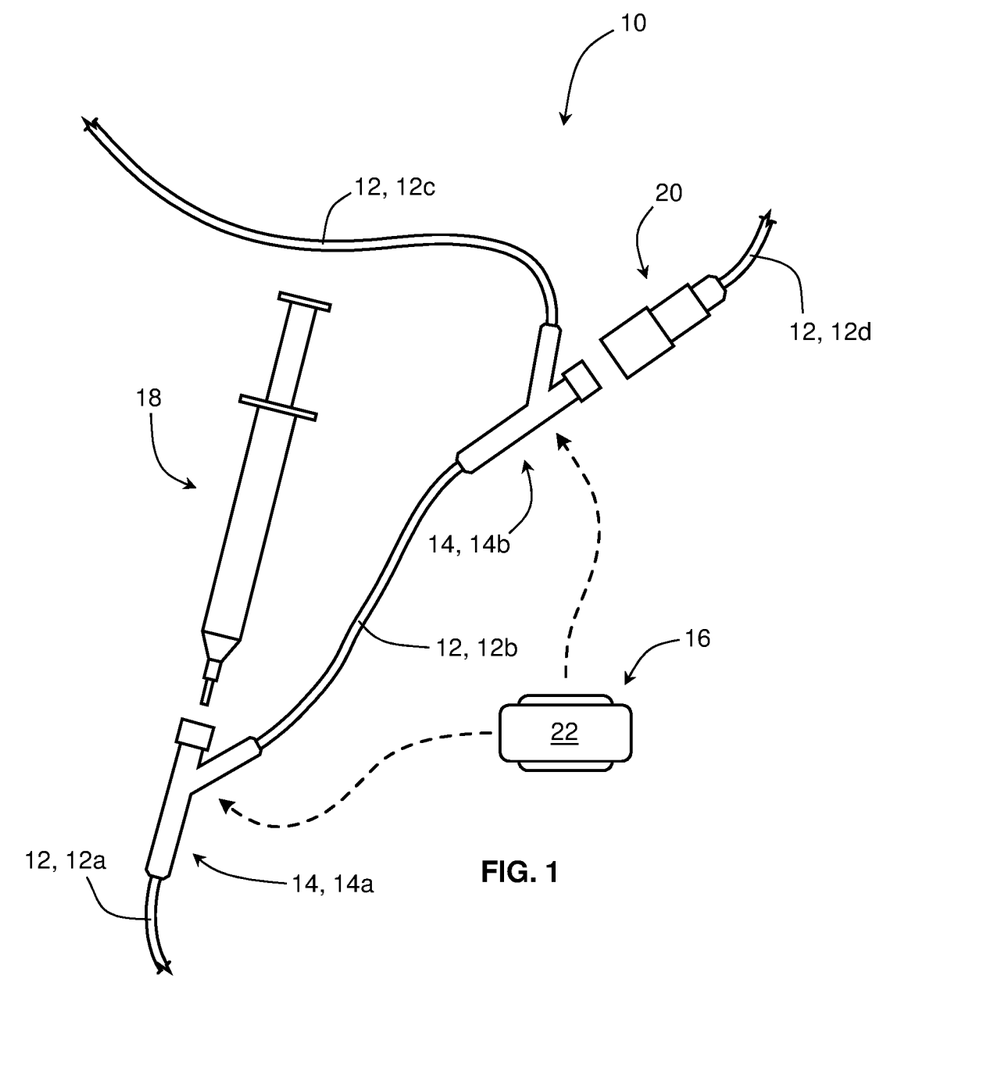
FIG. 1 is a schematic diagram showing an intravenous (IV) system in accordance with the present invention with a label in an uninstalled configuration.
Figure 2:
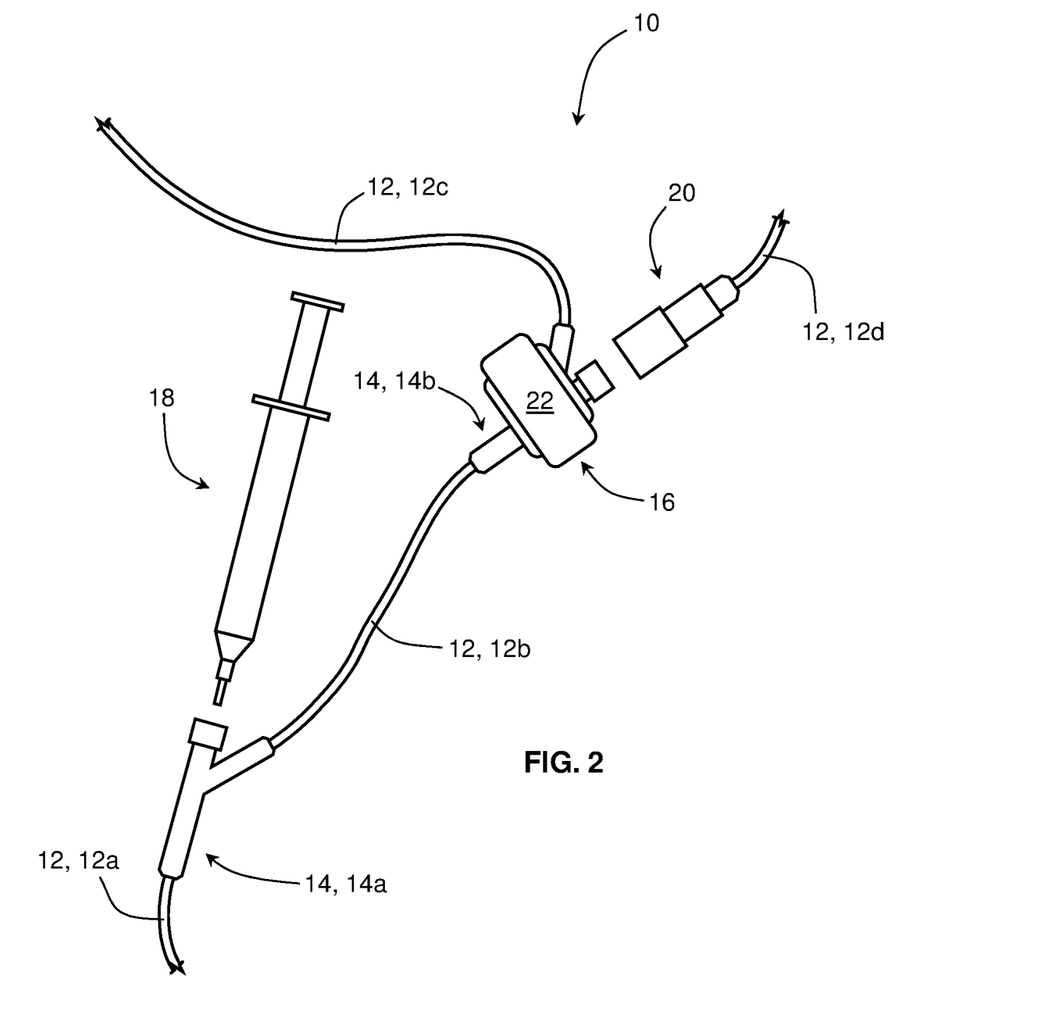
FIG. 2 is a schematic diagram showing the IV system of FIG. 1 with the label in an installed configuration.
Figure 3:
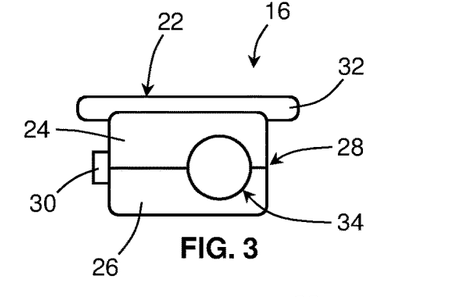
FIG. 3 is a schematic diagram showing a side view of the label of FIG. 1.
Figure 4:
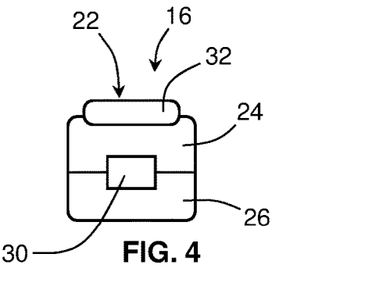
FIG. 4 is a schematic diagram showing an end view of the label of FIG. 1.

Referring to FIGS. 1 and 2, in selected embodiments, an IV system 10 in accordance with the present invention may include one or more sections of tubing 12, one or more access ports 14, and one or more labels 16. For example, in the illustrated embodiment, a first section of tubing 12*a* extends from a cannula (not shown) to a first access port 14*a*, a second section of tubing 12*b* extends from the first access port 14*a* to a second access port 14*b*, and a third section of tubing 12*c* extends from the second access port 14*b* to a primary IV solution bag (not shown). Accordingly, the first, second, and third sections of tubing 12*a*, 12*b*, and 12*c* may define or comprise the primary IV tubing.

The first and second ports 14a, 14b may enable other components to interact with the primary IV tubing. For example, one or more ports 14 (e.g., a first port 14a) may provide a location for one or more medications to be injected by a syringe 18 into the primary IV tubing. Alternatively or in addition thereto, one or more ports (e.g., a second port 14b) may provide a location for a "piggyback" attachment. A piggyback attachment may comprise a hub 20 suitable for engaging a port 14 and a fourth section of tubing 12d extending from the hub 20 to a secondary IV solution bag (not shown). Accordingly, an IV system 10 in accordance with the present invention may simultaneously and/or sequentially deliver a plurality of liquids, medications, or the like to a patient.

Certain liquids, medications, etc. may in some manner be incompatible with one another. Accordingly, it may be necessary to guard against a situation where a secondary liquid, medication, or the like is piggybacked onto a primary liquid, medication, or the like that is incompatible with the secondary liquid. In certain embodiments, a label 16 may provide a mechanism to guard against such a situation.

A label 16 may secure to a section of tubing 12, a port 14, or the like and provide a surface 22 on which identifying information may be written. For example, information identifying the liquid, medication, or the like corresponding to the primary IV solution bag may be written on a surface 22 of a label 16. Accordingly, seeing that identifying information, a medical professional may recognize that it would be unsafe to piggyback an incompatible liquid, medication, or the like onto that IV system 10.

A surface 22 may be configured to receive and retain the writing applied thereto. For example, a surface 22 may be finely texted (e.g., with a sand-blasted type finish) in order to receive and retain ink of a writing implement. Alternatively, a surface 22 may be smooth to receive and retain a sticker upon which a medical professional may write.

A label 16 in accordance with the present invention may be formed of any suitable material or combination of materials. In certain embodiments, a label 16 may be formed (e.g., injection molded as independent parts that are assembled together, injection molded as a single, monolithic unit, or the like) from a polymeric material. The color or colors of a label 16 may be selected to reduce the likelihood that it will be overlooked by a medical professional.

In certain embodiments, a label 16 may be shaped to minimize discomfort to a patient. For example, the exposed edges and corners a label 16 may be smooth and/or rounded. Accordingly, a label 16 may not tend to catch on things or scratch a patient.

Referring to FIGS. 3-6, in selected embodiments, a label 16 may be shaped to engage or lock onto a section of tubing 12, a port 14, or the like. For example, a label 16 may include a top 24, bottom 26, hinge 28, and lock 30 that enable a label 16 to selectively clamp over and grip a section of tubing 12, a port 14, or the like.

A top 24 may include a substrate 32 defining or supporting the surface 22. A hinge 28 (e.g., a living hinge) may pivotably connect a top 24 to a bottom 26. A hinge 28 may enable a top 24 to pivot with respect to a bottom 26 through a range a motion bounded at opposite ends by a fully closed position and a fully open position.

In selected embodiments, an aperture 34 formed in a top 24, bottom 26, or some combination thereof may enable a section of tubing 12, a port 14, or the like to extend between and be secured by a top 24 and a bottom 26 when they are in the fully closed position. Accordingly, a label 16 may close onto tubing 12, a port 14, or the like without pinching off, restricting, crushing, or otherwise adversely affecting the tubing 12, port 14, or the like or the operation thereof. A lock 30 may selectively hold a top 24 and corresponding bottom 26 in the fully closed position. Thus, a lock 30 may keep a label 16 secured to a section of tubing 12, a port 14, or the like. However, by releasing a lock 30, a label 16 may be easily removed.

In selected embodiments, a label 16 may be specifically shaped to engage or lock onto a port 14. A port 14 may have a branched or "T" shape. An aperture 34 of a label 16 may be shaped to match, track, overlay, wrap around, or otherwise engage all or some portion of that branched or T shape. Accordingly, the label 16 may lock onto the port 14 and be prevented from sliding up and down and/or rotating with respect to an underlying port 14. Thus, a label 16 may be securely attached to a port 14.

Additionally, secondary liquids, medications, or the like will typically be introduced at a port 14. Accordingly, by securing a label 16 to a port, the identifying information written on a surface 22 may be placed at a location where it is unlikely to be missed by a medical professional seeking to inject or piggyback a secondary liquid, medication, or the like into or on the system 10.

Figures 5, 6, 7:
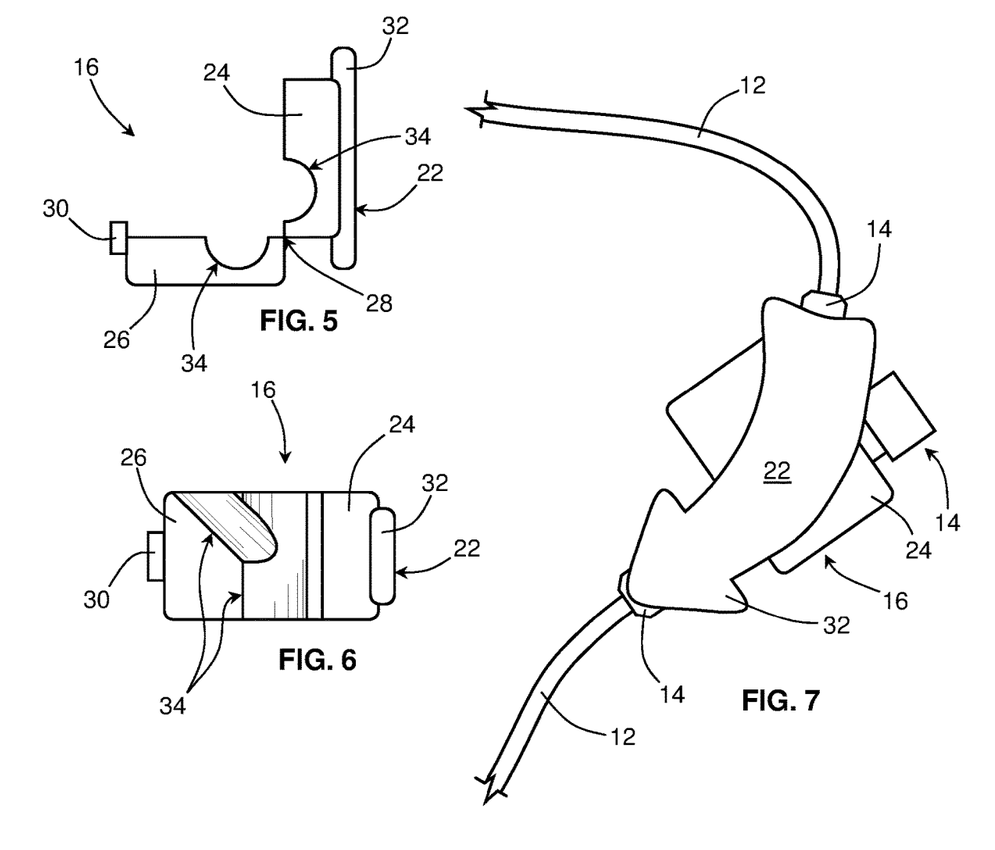
FIG. 5 is a schematic diagram showing a side view of the label of FIG. 1 with the top thereof pivoted to a vertical open position.
FIG. 6 is a schematic diagram showing a top view of the label of FIG. 1 with the top thereof pivoted to a vertical open position.
FIG. 7 is a schematic diagram showing a portion of an IV system in accordance with the present invention with an alternative embodiment of a label in an installed configuration.

Referring to FIG. 7, a substrate 32 and the surface 22 defined or supported thereby may have any suitable shape. In certain embodiments, a substrate 32 and corresponding surface 22 may be rectangular. Alternatively, a substrate 32 may have a less conventional shape. For example, a substrate 32 may have the shape of an arrow showing the direction of flow of a fluid (e.g., primary liquid or medication) through a port 14 to which the label 16 is applied. An outer surface of such an arrow may be the surface 22 upon which the name of the liquid or medication flowing in the indicated direction through the port 14 may be written.

Figure 8:
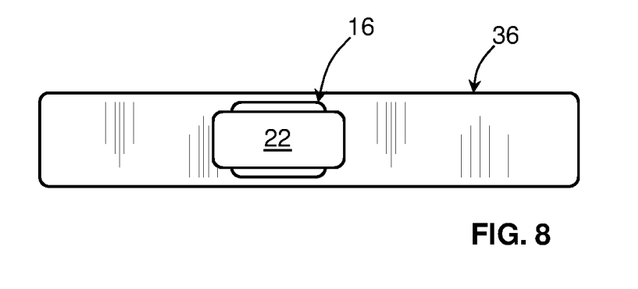
FIG. 8 is a schematic diagram showing a top view of a label secured to a securement mechanism in accordance with the present invention.
Figure 9:
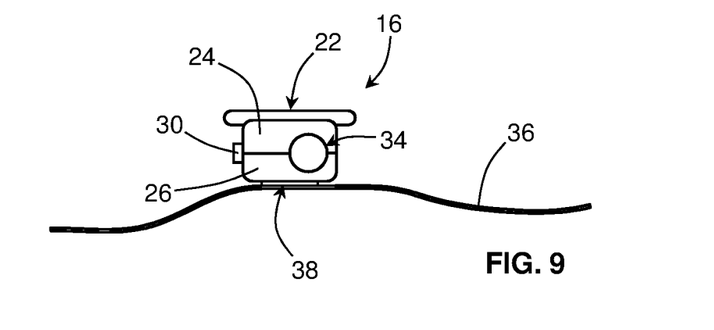
FIG. 9 is a schematic diagram showing a side view of the label and securement mechanism of FIG. 8.

Referring to FIGS. 8 and 9, in selected embodiments, a label 16 may be coupled to a securement mechanism 36. A securement mechanism 36 may be configured to engage or secure to a patient. For example, in certain embodiments, a securement mechanism 36 may comprise a flexible member with an adhesive applied to an underside thereof. Accordingly, a securement mechanism 36 may stick to the skin of a patient.

By securing a label 16 to a patient, a securement mechanism 36 may enable a label 16 in accordance with the present invention to function as an anchor for the tubing 12 and/or ports 14 of an IV system 10. Thus, a combination of a label 16 and securement mechanism 36 may prevent a cannula from being inadvertently pulled from a vein.

In selected embodiments, an interface 38 may connect a label 16 to a securement mechanism 36. The connection provided by an interface 38 may be initiated in a manufacturing process. That is, should a medical professional decide that a label 16 combined with a securement mechanism 36 is desired or needed, he or she may use such a combination as provided by a manufacturer. Alternatively, a label 16 and a securement mechanism 36 may be distributed as separate parts. Accordingly, should a medical professional decide that a label 16 combined with a securement mechanism 36 is desired or needed, he or she may select a label 16, select a securement mechanism 36, and use an interface 38 to effect an on-site connection between the two components 16, 36.

Figure 10:
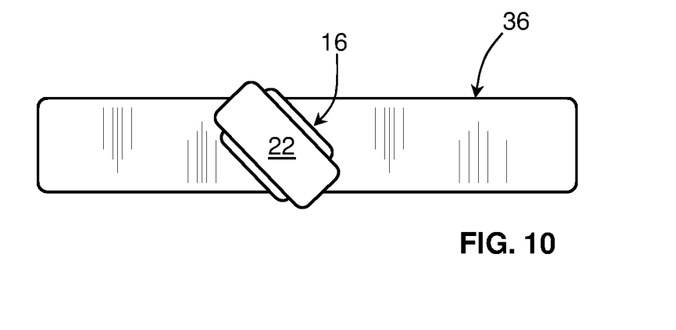
FIG. 10 is a schematic diagram showing a top view of the label and securement mechanism of FIG. 8 wherein the label is free to rotate with respect to the securement mechanism.

Referring to FIG. 10, in selected embodiments, an interface 38 may fix a label 16 with respect to a securement mechanism 36. Alternatively, an interface 38 may fix a label 16 with respect to a securement mechanism 36 only in certain directions or about certain axes. For example, in certain embodiments, an interface 38 may secure a label 16 to a securement mechanism 36 while permitting the label 16 to rotate with respect to the securement mechanism 36 about an axis (e.g., an axis extending normal to a particular section of the securement mechanism 36).

Figure 11:
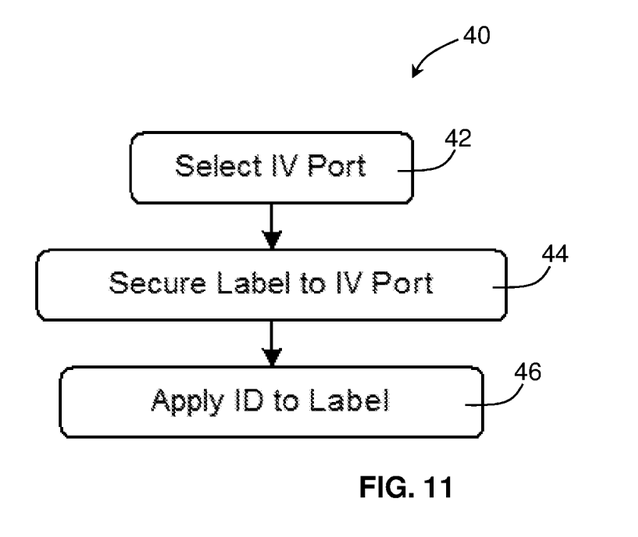
FIG. 11 is a schematic diagram of a method in accordance with the present invention.

Referring to FIG. 11, in certain embodiments, a method 40 in accordance with the present invention may include (1) selecting 42 an IV port 14, (2) securing 44 a label 16 to the IV port 14, and (3) applying 46 identifying information (e.g., information identifying the liquid, medication, or the like corresponding to the primary IV solution bag) to the label 16.

In selected embodiments, applying 46 identifying information to a label 16 may comprise writing on a surface 22 of the label 16. In other embodiments, applying 46 identifying information to a label 16 may comprise writing on a sticker adhered to a surface 22 of the label 16. In still other embodiments, applying 46 identifying information to a label 16 may comprise writing on a sticker and then adhering the sticker to a surface 22 of the label 16.

Figure 12:
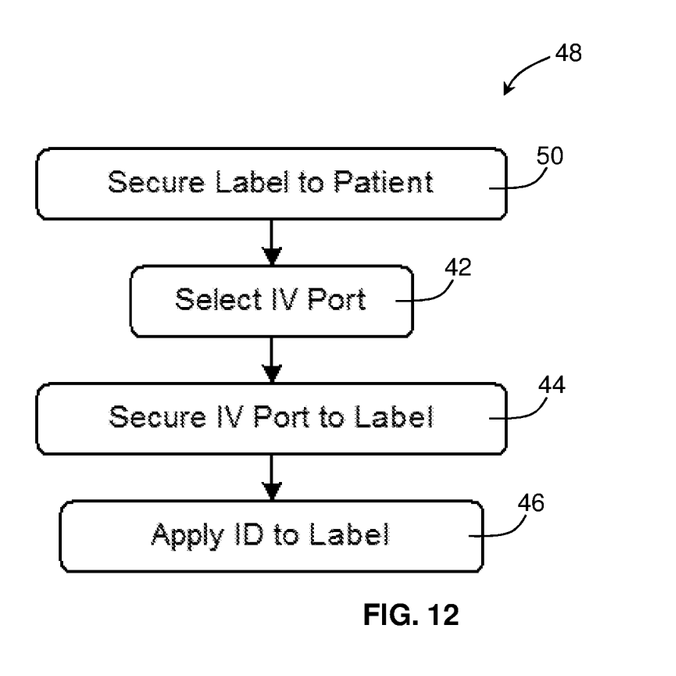
FIG. 12 is a schematic diagram of another method in accordance with the present invention.
Figure 13:
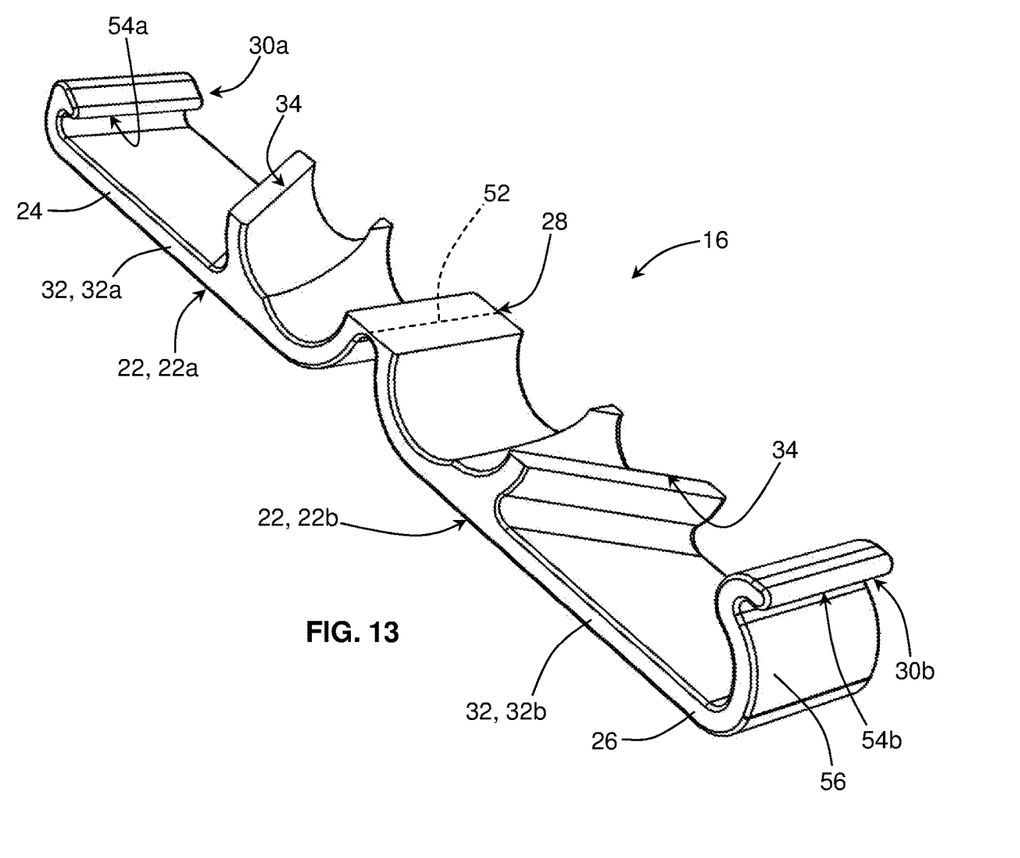
FIG. 13 is a perspective view of another alternative embodiment of a label in accordance with the present invention with the label is in an open, as-molded configuration.
Figure 14:
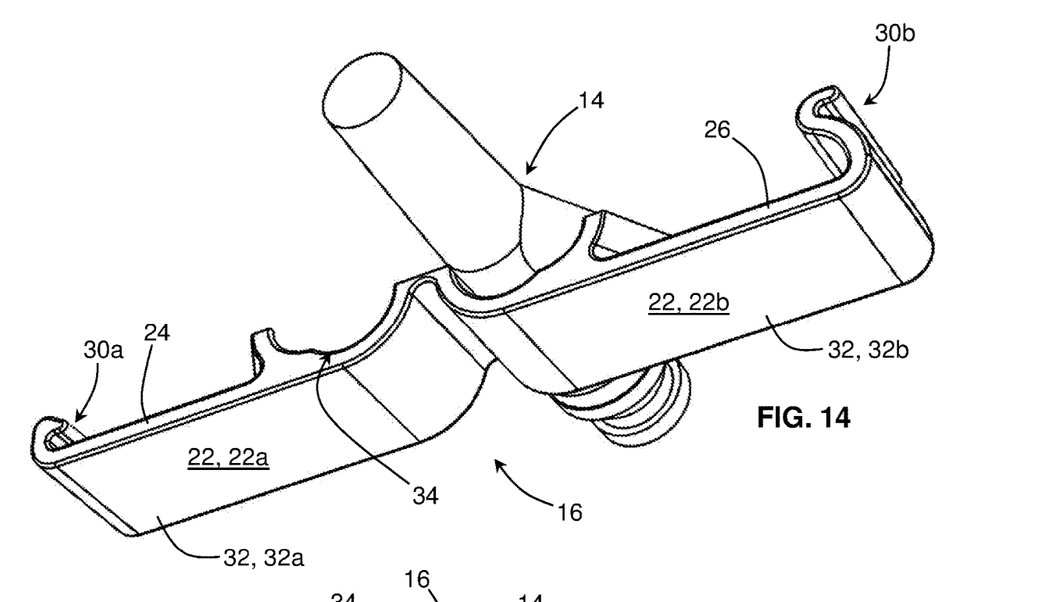
FIG. 14 is a perspective view of the label of FIG. 13 in an open configuration and with a port positioned therewithin in accordance with the present invention.
Figure 15:
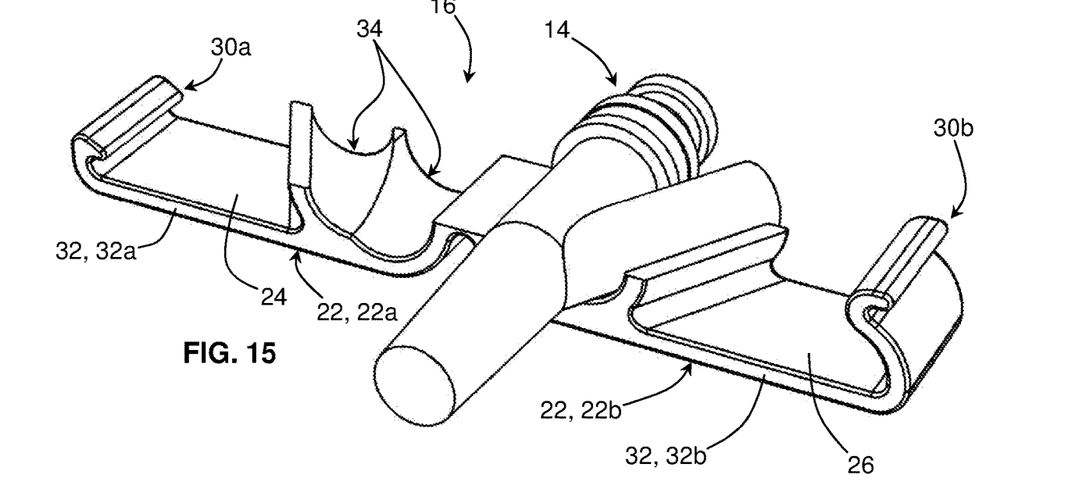
FIG. 15 is another perspective view of the label of FIG. 13 in an open configuration and with a port positioned therewithin in accordance with the present invention.
Figure 16:
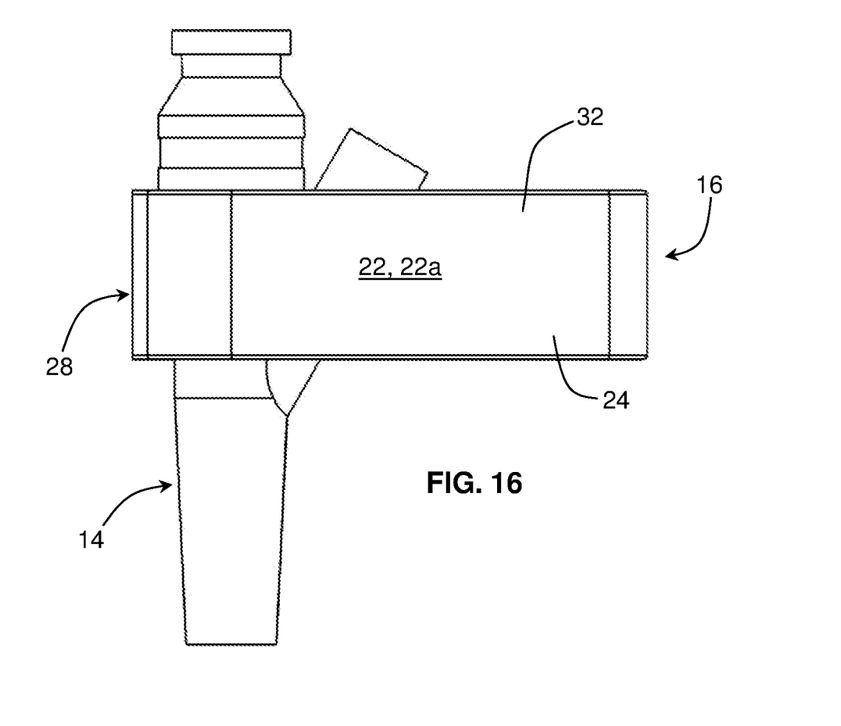
FIG. 16 is a side view of the label of FIG. 13 in an closed, folded configuration and with a port secured therewithin in accordance with the present invention.
Figure 17:
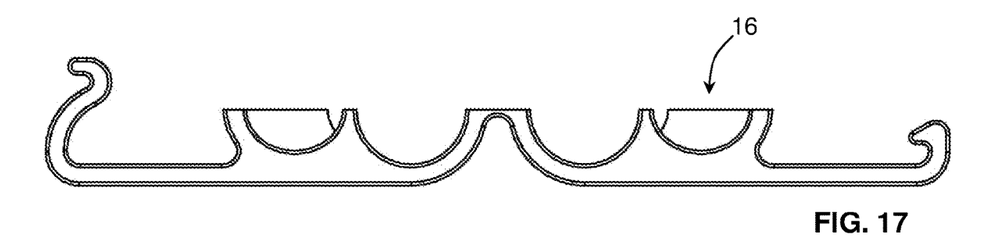
FIG. 17 is a top view of the label of FIG. 13 in an open configuration.
Figure 18:
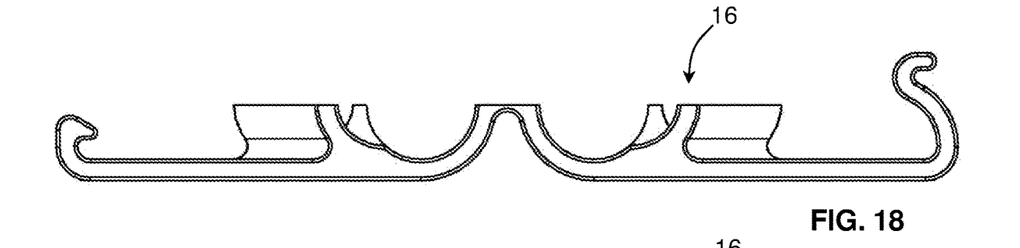
FIG. 18 is a bottom view of the label of FIG. 13 in an open configuration.
Figure 19:
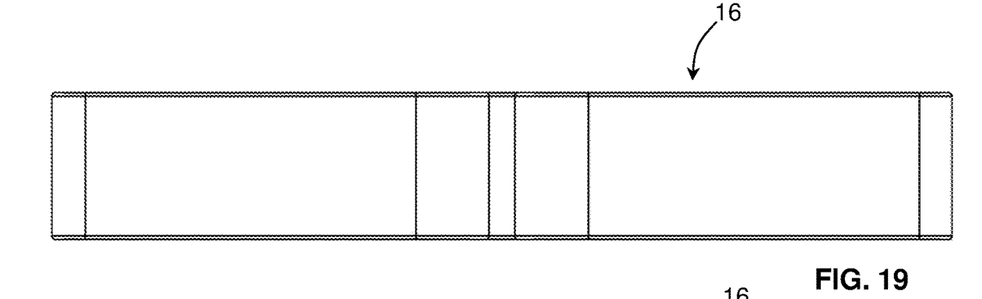
FIG. 19 is a first, exterior side view of the label of FIG. 13 in an open configuration.
Figure 20:
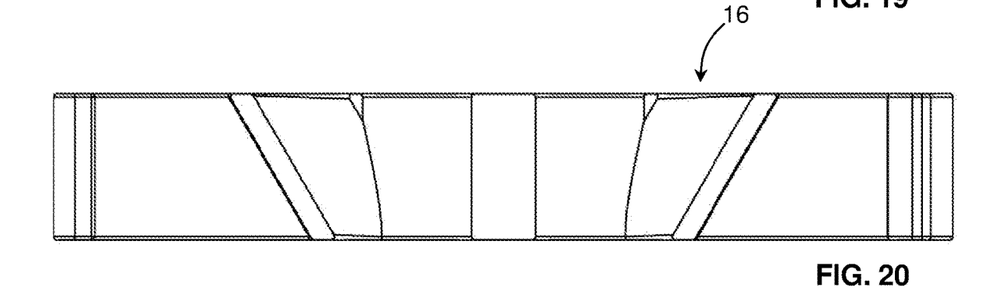
FIG. 20 is a second, interior side view of the label of FIG. 13 in an open configuration.
Figure 21:
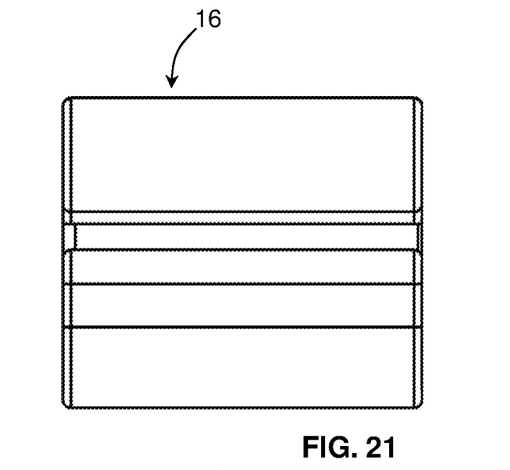
FIG. 21 is a first end view of the label of FIG. 13 in an open configuration.
Figure 22:
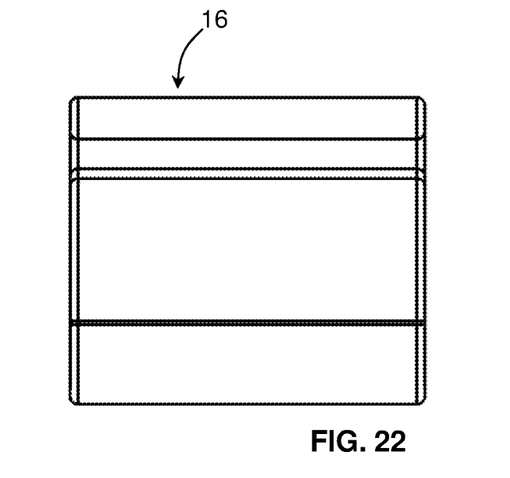
FIG. 22 is a second, opposite end view of the label of FIG. 13 in an open configuration.
Figure 23:
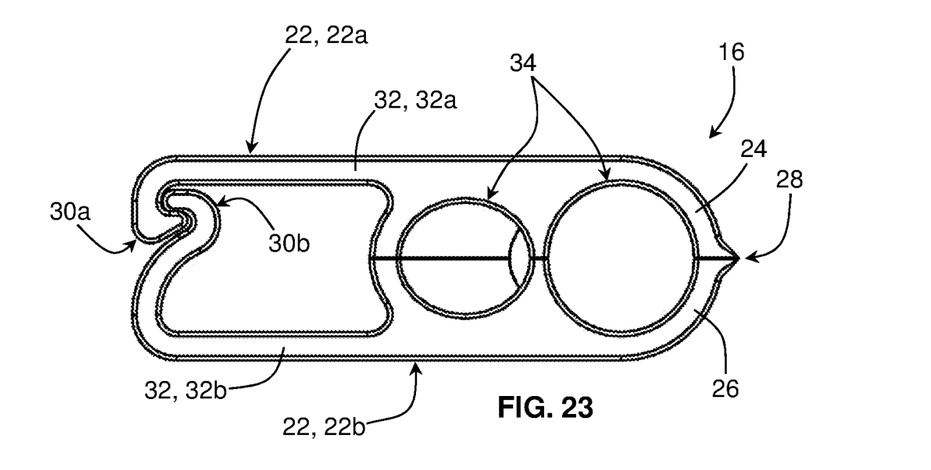
FIG. 23 is a top view of the label of FIG. 13 in a closed configuration.
Figure 24:
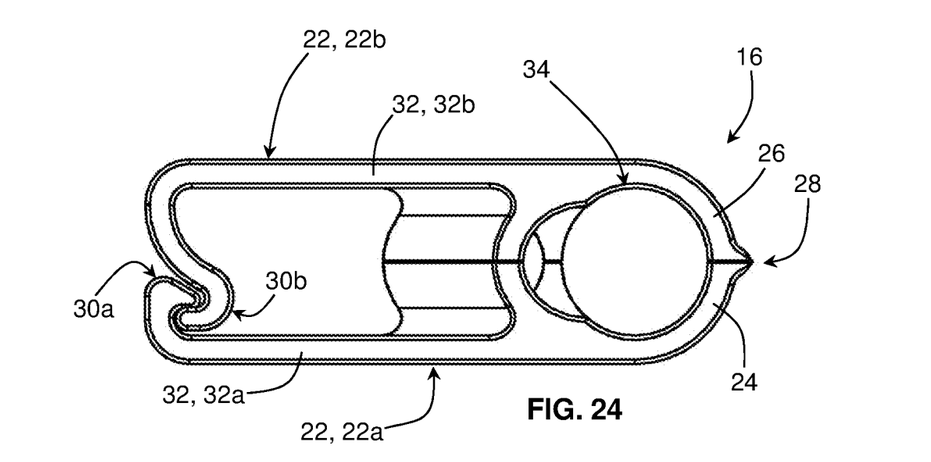
FIG. 24 is a bottom view of the label of FIG. 13 in a closed configuration.
Figure 25:
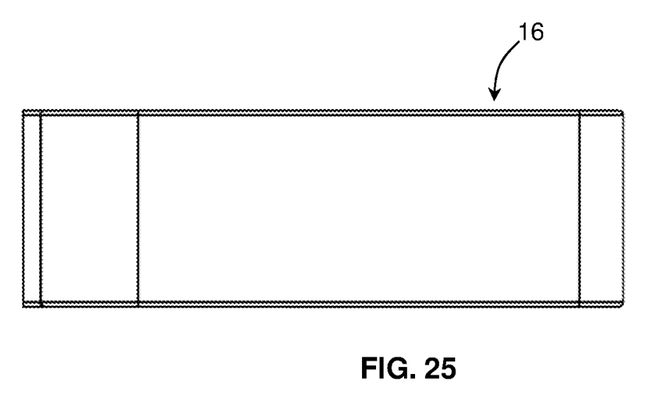
FIG. 25 is a first side view of the label of FIG. 13 in a closed configuration.
Figure 26:
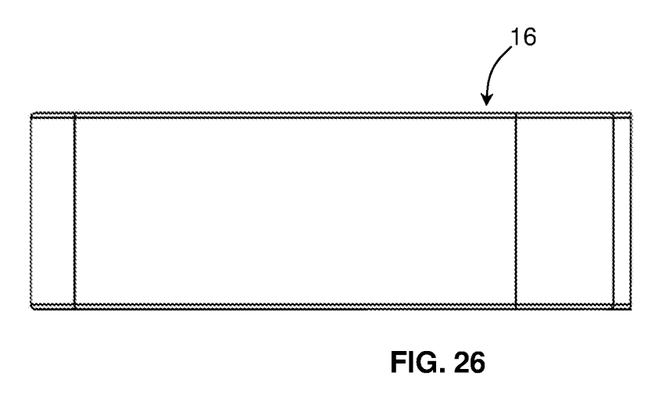
FIG. 26 is a second, opposite side view of the label of FIG. 13 in a closed configuration.
Figure 27:
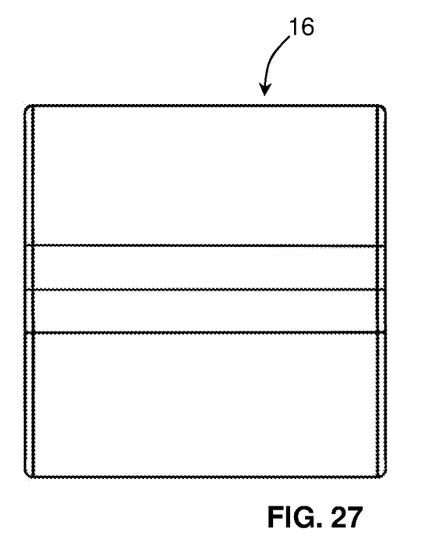
FIG. 27 is a first end view of the label of FIG. 13 in a closed configuration.
Figure 28:
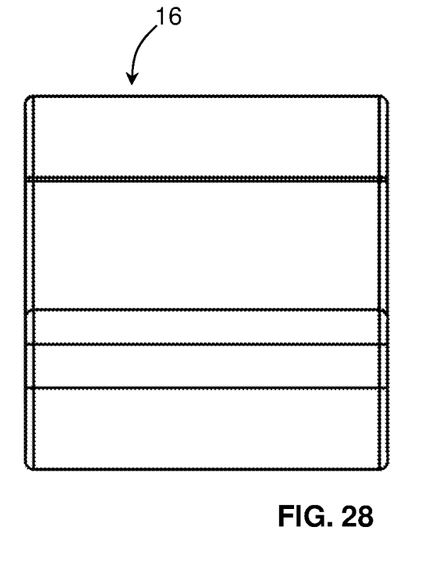
FIG. 28 is a second, opposite end view of the label of FIG. 13 in a closed configuration.

Referring to FIG. 12, in certain embodiments, an alternative method 48 in accordance with the present invention may include (1) securing 50 a label 16 to a patient, (2) selecting 42 an IV port 14, (3) securing 44 the IV port 14 to the label 16, and (4) applying 46 identifying information (e.g., information identifying the liquid, medication, or the like corresponding to the primary IV solution bag) to the label 16.

In selected embodiments, securing 50 a label 16 to a patient may include (1) selecting a combined label 16 and securement mechanism 36 and (2) applying the securement mechanism to the skin of a patient. In other embodiments, securing 50 a label 16 to a patient may include (1) selecting a label 16, (2) selecting a securement mechanism 36, (3) using an interface 38 to connect the label 16 to the securement mechanism 36, and (4) applying the securement mechanism to the skin of a patient.

It should be noted that, in some alternative implementations, the actions noted in the blocks may occur out of the order shown in FIGS. 11 and 12 and/or discussed hereinabove. In certain embodiments, two actions shown or discussed in succession may, in fact, be performed substantially concurrently, or the actions may sometimes be performed in reverse order, depending upon the functionality involved. Alternatively, certain steps or actions may be omitted if not needed.

Referring to FIGS. 13-28, in selected embodiments, a lock 30 may include a first engagement mechanism 30a and a second engagement mechanism 30b. A first engagement mechanism 30a may form part of a top 24 of a label 16. A second engagement mechanism 30b may form part of a bottom 26 of a label 16. In a closed position, a first engagement mechanism 30a may engage a second engagement mechanism 30b in order to secure a label 16 in the closed position. For example, in certain embodiments, as a label 16 transitions from an open configuration to a closed position (e.g., folds at a center line 52 to form a living hinge 28), a top 24 may pivot over onto a bottom 26 until an engagement is made between the first and second engagement mechanisms 30a, 30b.

In selected embodiments, first and second engagement mechanisms 30a, 30b may respectively include first and second shoulders 54a, 54b sized and positioned to overlap when a label 16 is in a closed position. In certain embodiments, a second shoulder 54b may be located on an end of an extension 56. Flexing of an extension 56 may enable a second shoulder 54b to pass around a first shoulder 54a to effect engagement and disengagement with the first shoulder 54a.

A label 16 may include multiple surfaces 22 (e.g., first and second surfaces 22a, 22b) suitable for writing. For example, in selected embodiments, a top 24 and bottom 26 may, with the exception of a lock 30 or various portions 30a, 30b thereof, be mirror images of one another. Accordingly, a top 24 and a bottom 26 may include respective substrates 32a, 32b (e.g., flat or substantially flat substrates 32a, 32b) having respective surfaces 22a, 22b on which a medical professional may write.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A method of labeling an intravenous (IV) system, the method comprising:
    selecting an access port of an IV system, the access port forming part of a junction where a first conduit of the IV system merges with a second conduit corresponding to the access port in a manner that places an interior of the first conduit in fluid communication with an interior of the second conduit;
    obtaining a label comprising
        a top having a first exterior writing surface,
        a bottom having a second exterior writing surface, and
        an aperture formed in at least one of the top and the bottom;
    applying the label to the junction by closing the top with respect to the bottom such that (1) the first exterior writing surface is substantially parallel to the second exterior writing surface, (2) both the first exterior writing surface and the second exterior writing surface are exposed, (3) the junction is secured within the aperture without blocking manual access to the access port, (4) structural interference between the label and the junction blocks the label from both rotating about the junction and sliding off of the junction, (5) the first conduit is located directly between the first exterior writing surface and the second exterior writing surface, and (6) a long axis of the label is perpendicular to the second conduit; and
    writing on at least one of the first exterior writing surface and the second exterior writing surface.

2. The method of claim 1, wherein the first exterior writing surface and the second exterior writing surface are both substantially flat and rectangular in shape.

3. The method of claim 2, wherein the label further comprises a hinge connecting the top to the bottom.

4. The method of claim 3, wherein the first exterior writing surface is substantially identical in size and shape to the second exterior writing surface.

5. The method of claim 1, wherein:
    the first exterior writing surface and the second exterior writing surface are both substantially flat;
    the first exterior writing surface and the second exterior writing surface both are rectangular in shape and have a length and a width; and a width of the label is substantially equal to the width of the first exterior writing surface and to the width of the second exterior writing surface.

6. The method of claim 1, wherein:
the first conduit is located on a first side of the second conduit;
the label comprises a hinge connecting the top to the bottom;
the hinge defines a hinge axis about which the top pivots with respect to the bottom; and
the applying the label to the junction further comprises positioning the label such that (1) the hinge is located on a second side of the second conduit that is opposite the first side and (2) the hinge axis extends perpendicular to the long axis of the label.

7. The method of claim 1, further comprising:
passing a liquid through the first conduit and into a vein of a patient; and
leaving, after the applying, the label free to move with the junction and independently with respect to the patient.

8. The method of claim 1, wherein a first half of the aperture is formed in the top and a second half of the aperture is formed in the bottom.

9. The method of claim 8, wherein:
the first half of the aperture and the second half of the aperture each comprise a first channel and a second channel;
the applying comprises positioning the first conduit within the first channel of both the first half of the aperture and the second half of the aperture; and
the applying further comprises positioning the second conduit within the second channel of both the first half of the aperture and the second half of the aperture.

10. The method of claim 9, wherein:
the first half of the aperture comprises a junction of the first and second channels thereof; and
the second half of the aperture comprises a junction of the first and second channels thereof.

11. The method of claim 1, wherein:
the first exterior writing surface and the second exterior writing surface are both substantially flat;
the first exterior writing surface and the second exterior writing surface are both rectangular in shape and have a length and a width; and
the applying comprises securing the label with respect to the junction such that the lengths of the first and second writing surfaces both extend parallel to the long axis of the label.

12. A method of labeling an intravenous (IV) system, the method comprising:
selecting an access port of an IV system, the access port forming part of a junction where a first conduit of the IV system merges with a second conduit corresponding to the access port and an interior of the first conduit is in fluid communication with an interior of the second conduit;
passing a liquid through the first conduit and into a vein of a patient;
obtaining a label comprising a first exterior writing surface and an aperture;
applying the label to the IV system by clipping the label to the junction such that (1) the junction is secured within the aperture without blocking manual access to the access port, (2) a long axis of the label is perpendicular to the second conduit, (3) the first exterior writing surface extends away from the second conduit and over the first conduit, and (4) structural interference between the label and the junction blocks the label from both rotating about the junction and sliding off of the junction;
writing medical information on the first exterior writing surface; and
leaving, after the applying and during the passing, the label free to move with the junction and independently with respect to the patient.

13. The method of claim 12, wherein the writing comprises writing a name of the liquid or a medication carried within the liquid.

14. The method of claim 12, wherein the label further comprises a second exterior writing surface that is substantially identical in size and shape to the first exterior writing surface.

15. The method of claim 14, wherein the label further comprises:
a top comprising the first exterior writing surface;
a bottom comprising the second exterior writing surface; and
a hinge connecting the top to the bottom, the hinge extending perpendicular to the long axis when the label is clipped to the junction.

16. The method of claim 15, wherein the applying comprises capturing the junction between the top and the bottom.

17. A method of labeling an intravenous (IV) system, the method comprising:
selecting an access port of an IV system, the access port forming part of a junction where a first conduit of the IV system merges with a second conduit corresponding to the access port and an interior of the first conduit is in fluid communication with an interior of the second conduit;
passing a liquid through the first conduit and into a vein of a patient;
obtaining a label comprising
a first exterior writing surface, and
an aperture having a first channel and a second channel that converges with the first channel, the first channel being shaped and sized to receive the first conduit therewithin, the second channel being shaped and sized to receive the second conduit therewithin;
applying the label to the IV system by clipping the label to the junction such that (1) the first conduit is secured within the first channel of the aperture and the second conduit is secured within the second channel of the aperture without blocking manual access to the access port, (2) a long axis of the label extends orthogonally with respect to the second conduit, and (3) the first exterior writing surface extends away from the second conduit and over the first conduit;
writing medical information on the first exterior writing surface; and
leaving, after the applying and during the passing, the label free to move with the junction and independently with respect to the patient.

18. The method of claim 17, wherein the writing comprises writing a name of the liquid or a medication carried within the liquid.

19. The method of claim 17, wherein:
the label further comprises a second exterior writing surface;
the applying comprises clipping the label to the junction such that the first exterior writing surface is positioned on one side of the label and the second exterior writing surface is positioned on an opposite side of the label;

the leaving further comprises leaving, after the applying and during the passing, both the first exterior writing surface and the second exterior writing surface exposed.

20. The method of claim 18, wherein the applying further comprises securing the label with respect to the junction such that the first conduit is located directly between the first exterior writing surface and the second exterior writing surface.

\* \* \* \* \*